Figure 1:
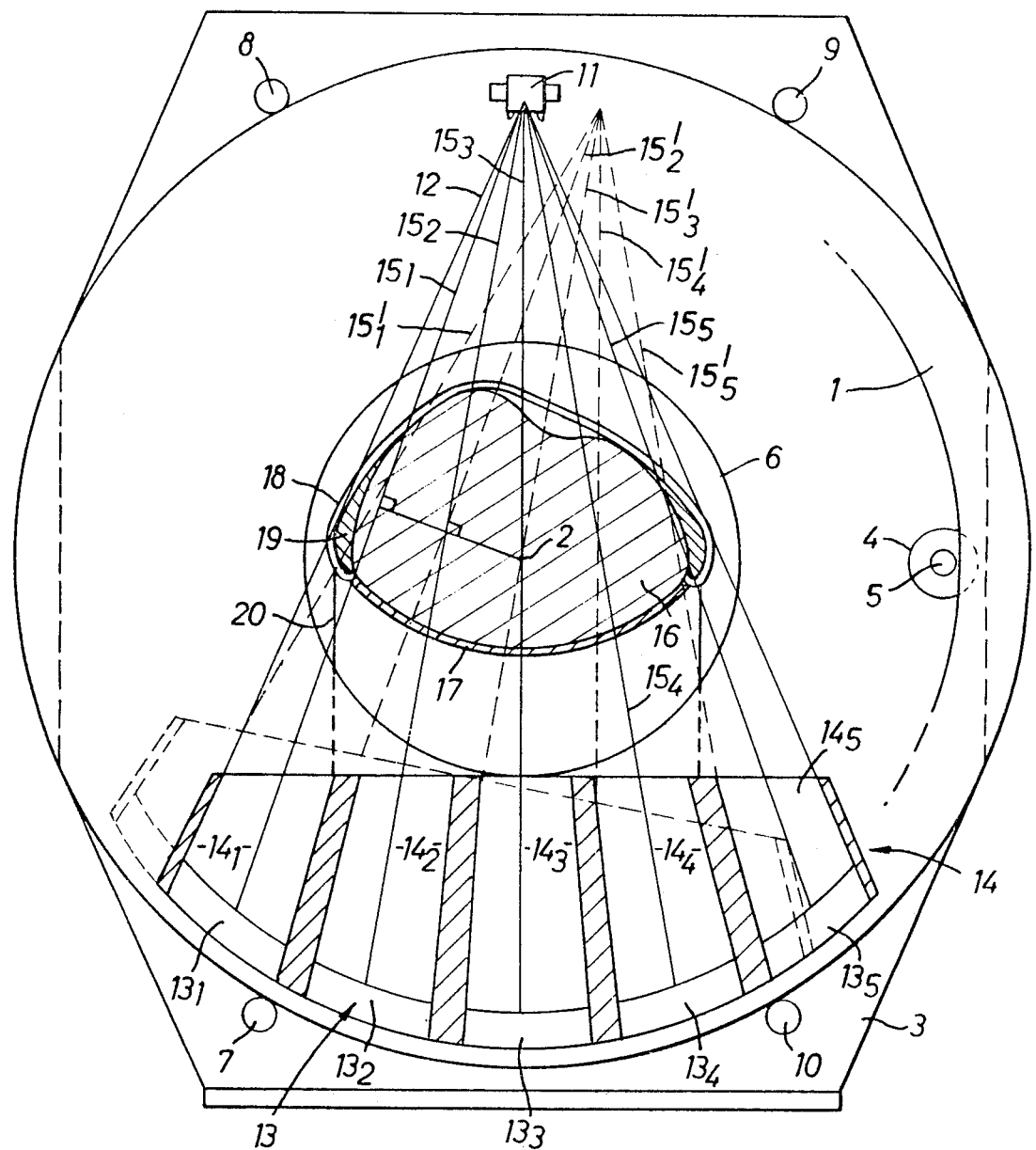

United States Patent [19]

Best et al.

[11] Patent Number: 4,843,618
[45] Date of Patent: Jun. 27, 1989

[54] RADIOGRAPHY

[75] Inventors: John E. Best, Oxon; Christopher A. G. LeMay, Osterley; Godfrey N. Hounsfield, Newark; Robert J. Froggatt, Southall, all of England

[73] Assignee: EMI Limited, Hayes, England

[21] Appl. No.: 486,375

[22] Filed: Apr. 19, 1983

Related U.S. Application Data

[63] Continuation of Ser. No. 936,880, Aug. 25, 1978, Continuation of Ser. No. 773,761, Mar. 2, 1977, abandoned.

[30] Foreign Application Priority Data

Mar. 4, 1976 [GB] United Kingdom ............... 8648/76

[51] Int. Cl.$^4$ ............................................. H05G 1/60
[52] U.S. Cl. ......................................... 378/4; 378/901; 364/413.18
[58] Field of Search ............................. 378/4, 19, 901; 364/414

[56] References Cited

U.S. PATENT DOCUMENTS 3,924,129 12/1975 LeMay .
3,934,142 1/1976 Hounsfield .
4,002,917 1/1977 Mayo .

Primary Examiner—Craig E. Church
Attorney, Agent, or Firm—Cooper & Dunham

[57] ABSTRACT

In a computerized tomographic apparatus in which the requisite absorption data are derived by rotating a source of fanned radiation around a body to be examined and detecting radiation emergent from a cross-sectional slice of the body at many times during the rotation the data, when assembled into sets relating to parallel beam paths through the slice, tends to relate to beam paths which are non-uniformly spaced across the slice. Some techniques for processing such data to produce a representation of the variation of absorption of said radiation over the slice should preferably have said data presented thereto in the form of sets relating to substantially uniformly spaced, parallel beam paths. The application of this invention provides considerably more data then is actually required for the processing so that data relating to beam paths of the required numbers and dispositions can be derived therefrom.

5 Claims, 2 Drawing Sheets

RADIOGRAPHY

This is a continuation of application Ser. No. 936,880, filed August 25, 1978, which in turn is a continuation of Ser. No. 773,761 filed on Mar. 2, 1977.

The present invention relates to radiography, and it relates more particularly to that branch of radiography which has become known as computerised axial tomography, or briefly C.A.T. Apparatus for performing C.A.T. has the aim of producing a representation of the absorption coefficients, with respect to penetrating radiation, at a plurality of elemental locations distributed over a cross-sectional slice of a body under investigation. Such apparatus is disclosed and claimed in U.S. Pat. No. 3778614.

The technique of performing C.A.T. involves deriving signals indicative of the absorption suffered by penetrating radiation, such as X-radiation, on transversing many beam paths through the slice of the body, in alignment with said slice. These signals are then processed to evaluate the aforementioned coefficients.

In order that the radiation may be projected through the slice along the many beam paths referred to above, it is usual to mount a source of the radiation and one or more detectors sensitive to the radiation at opposite sides of the body and to scan these components relative to the body in alignment with the slice. The scanning may comprise a combination of translational and rotational scanning movements both effected mechanically. If, however, it is desired to obtain the signals rapidly, the mechanical scanning may comprise only a rotational scanning movement, and in these circumstances the X-ray tube is constructed so that the radiation fans out therefrom, the angle of the fan being sufficient to irradiate at least a substantial part of the slice; the fan, of course, being aligned with the slice. An array of detectors is provided, the detectors being distributed across the breadth of the fan of radiation so that each receives radiation projected along a respective beam within the fan; the beams being equi-angularly spaced. As the source and the detectors are rotated relative to the body, each detector is repeatedly sampled at intervals which correspond to rotational movements corresponding to the inter-beam angle, and by this means a sequence of signals indicative of the absorption suffered by the radiation on traversing each of a group of beam paths is derived from each detector. The group of beam paths to which the signals derived from any one detector relate will not, of course, be parallel to one another; they will be angularly spaced from one another at substantially the aforementioned inter-beam angle. These paths will however be characterised by having a common perpendicular distance to the axis of the rotational scan, which axis is perpendicular to the plane of the region (and thus the spread of radiation) and passes through the body under examination.

It is convenient to process the signals derived from all of the detectors by means of the technique described and claimed in U.S. Pat. No. 3924129 but this technique is best applied to output signals relating to sets of equally spaced, parallel beam paths.

The signals obtained as described above can be sorted into sets relating to parallel beam paths; it being appreciated that the signals of a set are all derived from different detectors and obtained at different times during the scanning. However these beam paths are not equally spaced and when it is desired to evaluate the aforementioned coefficients with high accuracy, it has been found necessary to allow for this lack of equal spacing, which arises because the perpendicular distances to the axis of rotation for the various detectors vary in a substantially sinusoidal fashion from the axis outwards; the paths being more closely spaced towards the edges of the region of interest than they are at the centre thereof.

The object of this invention is to allow for the aforementioned inequality of beam spacing.

According to this invention there is provided radiographic apparatus including a source of penetrating radiation, such as X-radiation, radiation fanning out from said source to follow n mutually divergent beams, support means constraining said source to project said radiation through a cross-sectional slice of the body of a patient, scanning means for moving said support means, and with it said source, angularly around the body about an axis intersecting said slice, causing said radiation to project through said slice from a plurality p of different directions, detector means for receiving radiation emergent from said slice along each of said beams from each of said directions, sampling means for sampling said detector means to derive therefrom output signals relating to respective paths followed by said beams through said slice, the scanning means and the sampling means being adapted to produce output signals relating to a total of m beam paths, where m exceeds the product np at least five-fold and processing means for operating upon said output signals to produce modified signals which relate to a set of at least n parallel and substantially equally spaced beam paths disposed at each of at least p angles with respect to said body.

Figure 2:
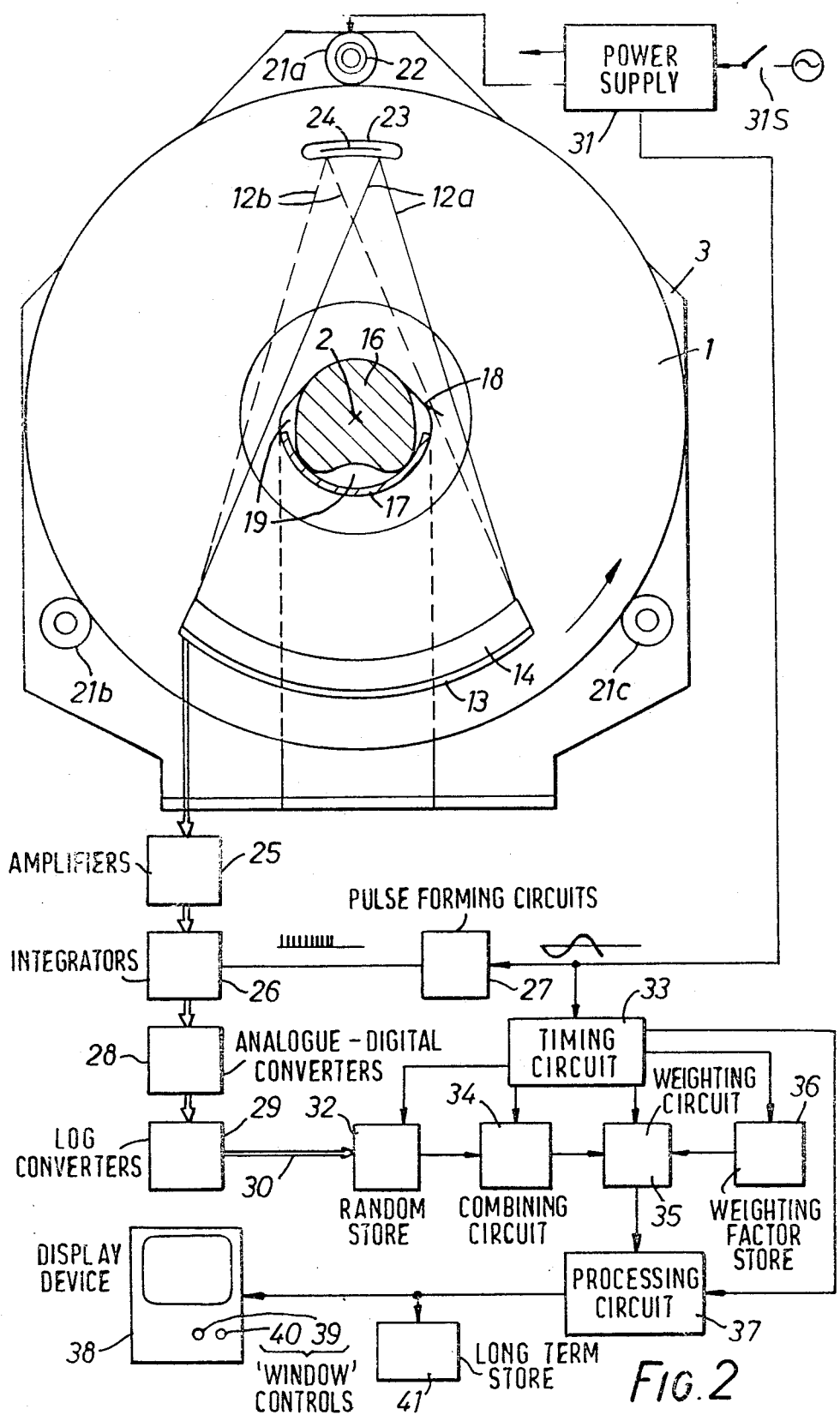

In order that the invention may be clearly understood and readily carried into effect, some embodiments thereof will now be described with reference to the accompanying drawings, of which FIG. 1 shows, in front elevational view, some of the components of a C.A.T. apparatus in which the only mechanical scanning movement is a rotational one, and shows how the aforementioned non-uniformity of spacing of parallel beam paths occurs, and FIG. 2 shows, in similar view to that in FIG. 1, apparatus in accordance with one example of this invention.

Referring now to FIG. 1, a ring-like rotatable support structure 1, is mounted for rotation about an axis 2. The structure 1 comprises an annular member which can be rotated relative to a static main frame 3 by an electric motor 4. The motor 4 is mounted on the main frame 3 and drives a gear wheel 5 which co-operates with gear teeth (not shown) formed all around the inner periphery of the ring-like structure 1. The main frame 3 has an aperture 6 formed therein, the aperture 6 being concentric with the ring-like structure 1, and also supports a number of guides 7, 8, 9, 10 which act as bearings during rotation of structure 1 about the axis 2 and thus support the load of that structure; the guides 7 through 10 being also formed with flanges to limit fore-and-aft movement of the structure 1.

The structure 1 supports an X-ray tube 11, arranged to produce a planar fan-shaped spread 12 of X-radiation, and a bank 13 of detectors, the detectors being sensitive to said radiation and being distributed across the breadth of the spread 12. It is stressed that the word "spread" as used herein in relation to X-radiation, is intended to encompass distributions of X-radiation which are not continuous. In particular, such distributions might comprise a plurality of individual, mutually divergent beams. The individual detectors, which may comprise thallium-activated sodium iodide crystals, are numbered $13_1$, $13_2$ ... $13_5$; only five detectors being shown in this case for clarity, although more typically, for a fan-shaped spread of angle 40° as shown, 120 detectors would be used, adjacent detectors being angled at ⅓° to each other. Each detector in the array 13 views the radiation source 11 through a respective collimator 14 so as to reduce the amount of scattered radiation received by the detectors, and thus each detector receives radiation along a respective beam 15 in the spread 12; the beams being indicated in the drawing by their centre lines, although it will be appreciated that the beams are actually of finite width, related to the collimator dimensions. It will also be appreciated that, in this example, the spread 12 is continuous across its breadth prior to its incidence upon the collimators 14.

The body 16 to be examined is supported on a bed 17 and held firmly thereon by means of a strap 18 secured to the sides of the bed. Packing material 19 is inserted in gaps between the body and the bed in order to reduce, so far as is possible, the entrapment of air between the patient and the bed. The material 19 is preferably contained in one or more flexible bags and absorbs the radiation to an extent similar to human body tissue. The bed is supported on either side of the main frame 3; one of the supports being shown at 20. It will be appreciated, of course, that the aperture 6 in the main frame 3 must be sufficiently large to enable the body 16 to be positioned as required relative to the spread 12.

As will be seen, when the structure 1 is in the position shown in the drawings, so that the source 11 projects the spread 12 of radiation through the body from the direction indicated in solid lines, each of the beams 15 traverses a respective path through the body 16, and the corresponding detector 13 provides an output signal indicative of the absorption suffered by the radiation on traversing the relevant path. In practice, an output signal relates not to a beam path as irradiated from a single point, but to a broader beam path irradiated during rotation of the structure 1 through a finite angle. This matter, however, will be ignored henceforth, because it is not relevant to the understanding of the invention, and it will be assumed that the output signals relate to beam paths irradiated at unique angular positions of the structure 1.

It will be observed that the various beams 15, and consequently the corresponding beam paths through the body, diverge from one another at equal angles and so the group of output signals obtained in any one position of the structure 1 do not relate to a parallel set of beam paths.

If the structure 1 is rotated through and angle corresponding to the angle between adjacent beams 15, so that the swath 12 assumes the position indicated by dotted lines, then the beams 15 will irradiate a new group of beam paths through the body 16. In this case, the beam path $15_2'$ viewed by detector $13_2$ from its new position is parallel with the beam path $15_1$ which was viewed by detector $13_1$ in its original position. Likewise the path $15_3'$ viewed by detector $13_3$ in its new position is parallel to the path $15_2$ viewed by detector $13_2$ in its original position, and so on. Further rotational movement of the structure 1 about the axis 2 causes the various detectors to provide output signals relating to beam paths parallel to paths for which output signals have previously been provided by other detectors.

As the mechanical movement is purely rotational, however, the beam paths of a parallel set are not uniformly spaced across the irradiated region of the body. This can be seen by comparing the perpendicular distance from the axis 2 to two parallel beam paths as irradiated by beams $15_1$ (detected by detector $13_1$) and $15_2'$ (detected by detector $13_2$), the structure 1 having rotated through an angle corresponding to the inter-beam angle between the irradiation of the two beam paths. If the distance from the point source of X-rays, within tube 11, to the axis 2 is designated r, and if the inter-beam angle is 10°, then the perpendicular distances from axis 2 to beams $15_1$ and $15_2'$ respectively are r sin 20° and r sin 10° respectively. Since the third beam of the parallel set in question will pass through the axis 2 and be detected by detector $13_3$ after the structure 1 has rotated through a further 10°, it will be seen that the values r sin 10° and r (sin 20° − sin 10°) represent the distances between respective pairs of beam paths in a parallel set and that these distances are not equal. Clearly the same thing will happen for beam paths on the other side of the axis 2 to those irradiated by beams $15_1$ and $15_2'$ and clearly also the non-uniformity of distance will be the same for all parallel sets of beam paths. For a fan angle of 40°, the overall departure from uniformity of spacing amounts to some 3% and, if it is desired to use a processing technique of the kind described and claimed in U.S. Pat. No. 3924129 and if it is desired to evaluate the aforementioned absorption coefficients with high accuracy, this departure must be allowed for.

One way in which the amount of data obtained could be increased in an apparatus of the kind shown in FIG. 1, to permit the selection of output signals relating to substantially uniformly spaced, parallel and co-planar beam paths through the body is simply to increase the number of detectors in the bank 13, using smaller detectors such as photo diodes to permit the increased number to be accommodated in the same angular extent, and to sample the output signals correspondingly more frequently.

A preferred technique, however, is one which not only provides additional data but also enables a check to be made on the relative sensitivities of the various detectors. Such techniques are described in U.S. Pat. No. 4,010,370 and U.S. Pat. No 4,115,698 and involve the source 11 being replaced by an X-ray tube of the kind in which the electron beam thereof can be scanned over a elongated anode therein so as to effectively shift the position of the spread of radiation relative to the rotatable structure 1. The scanning is effected in synchronism with the angular movement of structure 1 and the output signals derived from the various detectors are sampled several times (for example from ten to fifty times) during each scan of the electron beam over the anode.

Apparatus of the kind shown in the aforementioned U.S. Pat. No. 4,115,698 shown in FIG. 2, in which components similar to those in FIG. 1 have been allocated the same reference numerals. The body 16 to be examined, shown in transverse section, is supported on a suitably shaped bed 17 also shown in transverse section. As before, a material 19, having an absorption to the radiation similar to that of body tissue, is positioned between the body 16 and bed 17, to substantially exclude air from the gap therebetween, and is extended partly about the body, to provide an approximately circular cross-section to the radiation. The body is retained firmly in the desired position by means such as a retaining strap 18. If desired a more rigid retaining ring, such as the two part ring described in U.S. Pat. No. 3937963 may be used.

The bed 17 and the body 16 are inserted into an aperture in a rotatable member 1 so that a desired part of the body is centred in the aperture. The rotatable member 1 is arranged to rotate about an axis 2, longitudinal of the body and perpendicular to the paper, central to the aperture. For that purpose it is supported by three gear wheel 21, a, b, c, which engage with gear teeth, not shown, cut into the periphery of member 1. The gear wheels 21 are journalled in a main frame 3 of the apparatus, which may take any form suitable to support the apparatus and to allow the necessary rotation. Gear wheel 21a is driven by a synchronous electric motor 22, also mounted on the frame, the operation of which will be described hereinafter.

The rotatable member 1 also carries a source of X-rays 23, a bank of detectors 13 and associated collimators 14. The detectors, which in a typical embodiment number 120, can be of any suitable type for example scintillation crystals with associated photomultipliers or photodiodes.

The source 23 is of the type which includes an elongated target/anode 24 and provides a fan shaped spread 12 of X-rays from a substantially point origin which can be scanned by electronic means from the position 12a to the position 12b shown. In this example the corresponding scan of the substantially point origin of the X-rays along target 24 is of the order of 10 cm although it may be less if desired. The collimators have longitudinal axes which intersect at the centre of the anode 24.

Correspondingly the X-ray source 23 is placed of the order of 50 cm from the central axis 2 with the detectors 13 being placed a further 50 cm on the opposite side of axis 2 so as to intercept the radiation of fan 12 for any position of the point of origin of the X-rays in its lateral scan along target 24. If desired however the distance from source to axis 2 and detectors to axis 2 may be unequal without departing from the principles of the invention. It should be understood that collimators 14 are of dimensions which allow such interception while preventing the reception of scattered radiation to the greatest degree practically possible.

Disregarding for the moment the rotary motion referred to hereinbefore, the arrangement is such that the point of origin of the X-rays is scanned steadily along target 24 taking the fan of X-rays from 12a to 12b, and is rapidly returned to the starting point before repeating the scan. During the time of one such scanning movement each detector of array 13 provides an output signal indicative of the intensity of radiation incident thereon. For a given detector, these outputs are amplified in an amplifier 25 and then input to an integrator 26. There the output signals are integrated over periods determined by a series of pulses from pulse forming circuits 27. In this example the timing of the pulses is such that there are twelve integration periods in the time of one lateral scan of X-ray fan 12 from 12a to 12b. Thus each detector measures radiation, in effect, along twelve narrow beam paths joining that detector with twelve equally spaced positions along target 24. The paths are, of course, of width determined by the integration intervals and are of a shape determined by the geometry of scanning movements in those intervals. For the purpose of illustration, however, they may be considered to be represented by single lines which are in fact their centre lines. Thus the lines illustrating the extremes of fan 12 are in fact the centre lines of the extreme beams of the fan. Signals representing the intensity of radiation received along such paths are converted to digital form in converters 28 and to logarithmic form in converters 29 for output at 30 for further processing. It will be understood that one amplifier 25, integrator 26, A/D converter 28 and log converter 29 is provided for every detector, all operated in synchronism. The processing is effective to sort the signals into sets representing absorption along sets of parallel paths, as explained in U.S. Pat. No. 4,206,359 for processing by a suitable method such as that described in U.S. Pat. No. 3924129 to provide the desired representation. The circuits 25 to 29 are of well known construction.

In operation, motor 22 provides a continuous motion of rotatable member 1 and all the equipment mounted thereon, about an axis 2 and therefore about the body 16 of the patient on bed 17. The rotary motion and the lateral scanning of X-ray fan 12 must be in strict relationship to achieve the desired result. Synchronous motor 22 is driven by a periodic sinusoidal voltage from a power supply 31 and, after a suitable period of time, stabilises in synchronisation with sinusoidal voltage. It will be appreciated that, when under load, the motion of motor 22 lags the phase of the sinusoidal voltage but this in not significant provided the load does not change and therefore the lag is constant. The sinusoidal voltage from supply 31 is supplied to a time base generator (not shown) where it provides a periodic saw-tooth waveform voltage, to operate the scanning of source 23, and also to unit 27 which converts it to square pulse of the same phase and generates therefrom the series of pulses, in strict phase relationship with the sinusoidal voltage, to clear and read integrators 26 as explained hereinbefore. Pulse forming circuit 27 operates in a conventional manner by any suitable means known in the art. Flyback of the sawtooth waveform takes place during selected resetting periods of the integrators.

As an alternative to the circuits 27 a circular graticule may be used in the form of a translucent ring, co axial with and mounted on rotary member 1 and carrying engraved lines. The lines can interrupt a light path between a light source and photocell mounted, for example, on frame 3, so that the photocell provides pulses indicative of the movement of member 1. These pulses may be used both to operate the integrators 26 and to control the X-ray source 23.

Such a graticule arrangement would, of course, directly indicate the progress of the orbital scan and therefore be insensitive to changes of loads on the motor 22. In that case motor 22 need not be a synchronous motor. When operated in accordance with an example of the present invention, the apparatus shown in FIG. 2 is arranged to provide considerably more data than is required for accurate evaluation of the aforementioned absorption coefficients. Thus if the required data are characterised by n equally spaced beam paths at each of p angular dispositions in the body, the apparatus is arranged to provide m samples where m is at least five times, and possibly one hundred or one thousand times, larger than the product np.

When all of the m samples have been obtained, they relate to such a considerable number of beam paths that it is possible to designate beam paths for which data are required, i.e. beams paths which comprise the required number of uniformly distributed sets, and to combine a respective group of the samples to provide an absorption value applicable to each designated beam path; the group of samples so combined in any case being selected because of their proximity to the designated beam path in question. As previously mentioned, this expedient not only overcomes the problem of non-uniform spacing of sampled beam paths but also improves the accuracy of the apparatus because each combined group of samples is derived from a plurality of different detectors, and thus inter-detector sensitivity variations are not as serious as they are in a case where an output signal for a given beam is derived from one detector only.

The aforementioned combination of selected groups of samples to form absorption values for designated beam paths is achieved, in this example of the invention by applying the signals derived from the log converter circuits 29 to a random access digital store 32, deriving the signals from the store, under the influence of a timing circuit 33, in groups for combination and combining the groups in a combining circuit 34. In some cases it happens that certain designated beams run adjacent less samples than other designated beams. This, however, is known in advance from the geometry of the apparatus and is allowed for by normalisation, using a post-combination weighting circuit 35 which weights each combined value in accordance with the number of samples which it contains. The weighting factors used are held in a store 36 and fed to the circuit 35 under the control of the timing circuit 33 at the appropriate times to weight the proper combined values.

The data so corrected are applied to a processing circuit 37, of the kind described in the aforementioned U.S. Pat. No. 3924129 which processes the absorption values to evaluate the aforementioned absorption coefficients. The coefficients so evaluated are displayed on a suitable cathode ray tube device 38, which has facilities indicated by control knobs 39 and 40 for adjusting the extent and the absolute position of the dynamic range of coefficients displayed thereby. Such adjustments are commonly known as "window" adjustments.

The evaluated coefficients are also stored a magnetic tape or disc apparatus 41 so that they can be studied at a later date if required.

What we claim is:

1. Radiographic apparatus including a source of penetrating radiation, such as x-radiation, fanning out from said source to simultaneously follow n mutually divergent beams, support means constraining said source to project said radiation through a cross-sectional slice of the body of a patient with said n beams distributed across substantially the entire width of said slice, scanning means for moving said support means, and with it said source, angularly around the body about an axis intersecting said slice, causing said radiation to project through said slice from different directions, detector means for receiving radiation emergent from said slice along each of said beams from each of said directions, said detector means being supported by said support means and moved angularly around said body by said scanning means, sampling means for sampling said detector means during the angular movement of said source and said detector means around the body, to derive therefrom output samples relating to respective paths followed by said beams through said slice, the scanning means and the sampling means being adapted to produce output samples relating to a total of m beam paths, and processing means for operating upon said output signals to combine the samples into groups to thereby provide an absorption value applicable to each designated beam path of a set of at least n parallel and substantially equally spaced designated beam paths disposed at each of at least p angles with respect to said body, m exceeding the product np at least five-fold, and said processing means combining a respective plurality of said output samples to produce each of said absorption values.

2. Apparatus according to claim 1 including means for normalizing each of said absorption values to allow for the fact that some of said absorption values may contain contributions from more of said output samples than others of said absorption values.

3. Apparatus according to claim 1 including means for processing said modified signals to produce a representation of the variation of absorption coefficient, with respect to said radiation, from element to element over said slice.

4. Apparatus according to claim 1 wherein said source of radiation includes an x-ray tube having an elongated anode, and said scanning means includes means for selectively causing said radiation to fan out from various positions along said anode.

5. Apparatus according to claim 4 wherein said scanning means includes deflection means for sweeping the electron beam of said tube to and fro along said anode during said angular movement of said source around said body, the sweeping of said electron beam being carried out at a rate high compared with that of said angular movement and causing said radiation to fan out from said various positions along said anode.

* * * * *